(12) United States Patent
Skvirsky et al.

(10) Patent No.: US 9,655,696 B2
(45) Date of Patent: May 23, 2017

(54) KIT AND METHOD FOR TAKING DENTAL IMPRESSIONS AND FORMING DENTAL MODELS

(71) Applicant: Skvirsky Ltd., Bnei Brak (IL)

(72) Inventors: Igor Skvirsky, Givat-Koah (IL); Leonid Monassevitch, Hadera (IL); Yaniv Skvirsky, Givat-Koah (IL)

(73) Assignee: Skvirsky Ltd., Bnei Brak, IL (US)

( * ) Notice: Subject to any disclaimer, the term of this patent is extended or adjusted under 35 U.S.C. 154(b) by 311 days.

(21) Appl. No.: 14/515,300

(22) Filed: Oct. 15, 2014

(65) Prior Publication Data
US 2016/0106523 A1      Apr. 21, 2016

(51) Int. Cl.
*A61C 8/00*      (2006.01)

(52) U.S. Cl.
CPC .......... *A61C 8/0001* (2013.01); *A61C 8/0081* (2013.01)

(58) Field of Classification Search
CPC .... A61C 8/0048; A61C 8/0001; A61C 8/0081
See application file for complete search history.

(56) References Cited

U.S. PATENT DOCUMENTS

| | | | |
|---|---|---|---|
| 5,904,483 A * | 5/1999 | Wade | A61C 8/0048 433/173 |
| 6,540,515 B1 | 4/2003 | Tanaka | |

\* cited by examiner

*Primary Examiner* — Glenn Richman
(74) *Attorney, Agent, or Firm* — Avery N. Goldstein; Blue Filament Law PLLC

(57) ABSTRACT

A first assembly is provided for forming the dental impression and a second assembly for forming the dental model, wherein the first assembly includes an impression post; a first coupler for coupling the impression post with a dental implant affixed within the mouth; and an impression cap for positioning on the impression post. The second assembly includes: a model post; a second coupler for coupling the model post with a dental analog; and the impression cap. The impression cap has a first and second securing means, both for selectively securing the impression cap to the impression post and to the model post.

11 Claims, 5 Drawing Sheets

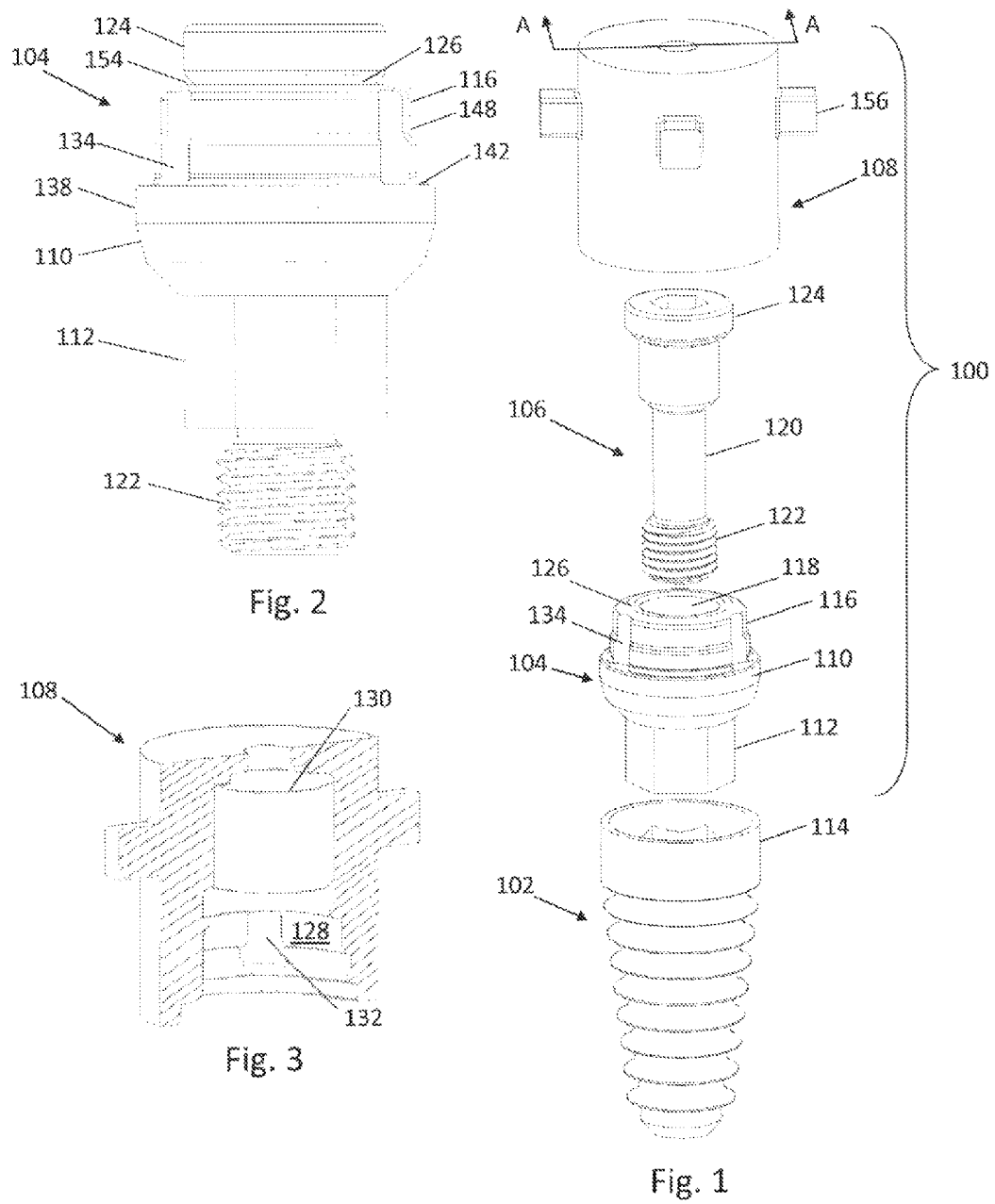

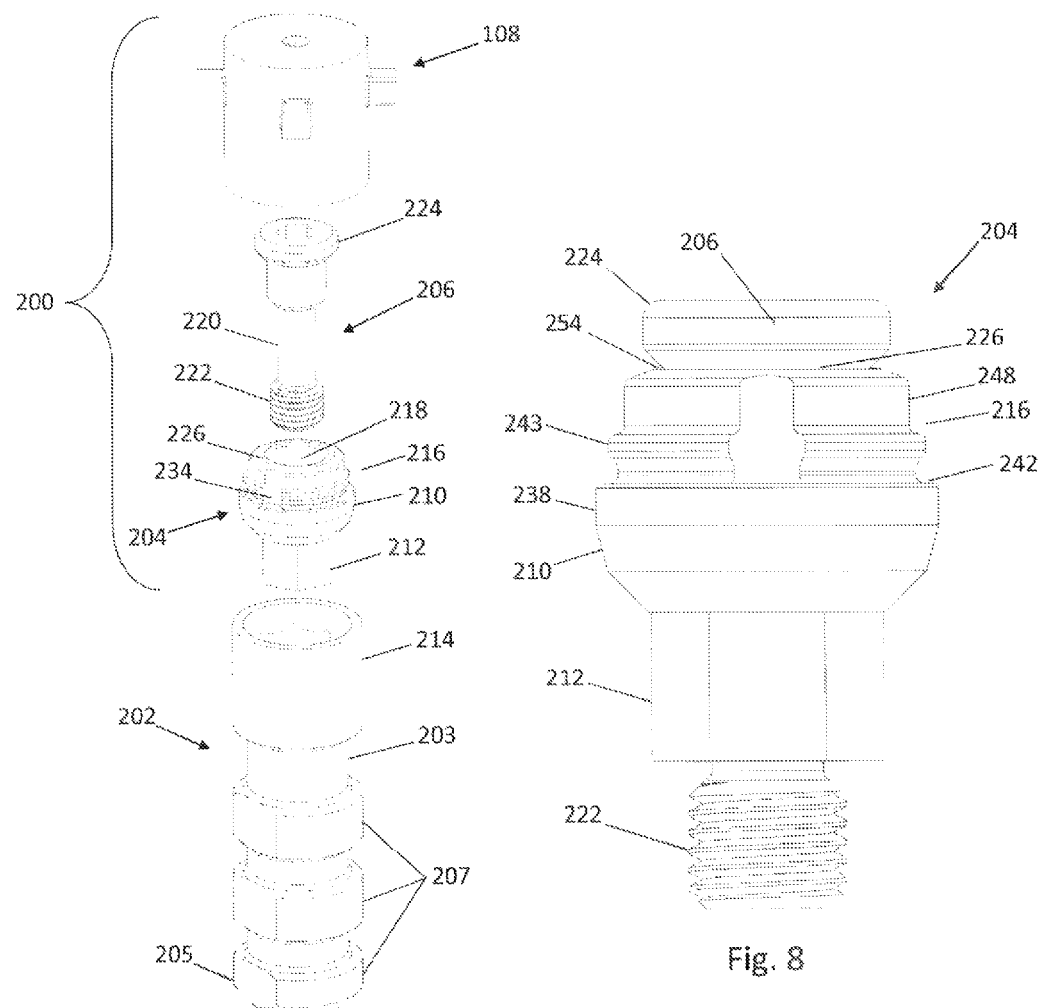

KIT AND METHOD FOR TAKING DENTAL IMPRESSIONS AND FORMING DENTAL MODELS

FIELD OF THE INVENTION

The present invention relates to the field of dentistry. In particular, the present invention relates to the procedures performed prior to the fabrication of prosthetics such as custom dentures supported by dental implants. More particularly, the present invention relates to a novel kit of dental components utilized to take dental impressions and to form dental models.

BACKGROUND OF THE INVENTION

The traditional technique for taking dental impressions and forming stone dental models is well known. Briefly, the procedure comprises inserting impression posts into one or more dental implant wells, positioning an impression cap on each impression post, placing impression material around the impression caps (either via injecting the material at the desired locations or positioning an impression tray with impression material around the caps), waiting until the impression material hardens and withdrawing the impression material with the caps embedded therein. The posts remain in the implant wells and are then removed individually. A dental analog is then inserted into each impression cap and a stone model is formed around the dental analogs.

A number of drawbacks are associated with the prior art components utilized for taking dental impressions and forming stone dental models. For instance, often the orientation of the dental implants within the mouth of a patient are not vertical, but rather are at non-orthogonal angles. Due to the length of the standard impression post and the angles of adjacent implants, it is often the case that the insertion of impression posts interfere with each other. Furthermore, difficulty is added to the withdrawal process when lifting the impression off of the gums at an essentially orthogonal angle, with caps embedded therein at non-orthogonal angles. In addition to the difficulty, caps may be dislodged or shifted within the impression material during the withdrawal process, resulting in misaligned prosthetics.

U.S. Pat. No. 6,540,515 to Tanaka discloses a magnetic attachment used for retaining a dental prosthesis, comprising a male part which may be fixed to an abutment and a female part which may be fixed to said dental prosthesis. The male part of the magnetic attachment includes a head portion, which may be attached to the female part, and a fixing member used for fixing the male part to said abutment. The female part includes a cap portion having a cover portion for covering the male part.

Magnetic attachment systems have advantages over mechanical attachment systems in that excessive stress on the implants at the time of the removal of the dental impression are reduced, as is the difficulty involved in the withdrawal process.

However, prior art magnetic attachment systems and methods, while provide a benefit when used for taking dental impressions, have drawbacks when forming a stone model around dental analogs. That is, when forming a stone model the analog is often easily moved due to its length and the moments generated by the force applied on it, thereby decreasing the accuracy of the replica.

SUMMARY OF THE INVENTION

Accordingly, it is a principal object of the present invention to provide a kit of dental components utilized in the formation of dental impressions as well as dental models, which overcomes the difficulties and drawbacks associated with the prior art, comprising a first assembly for forming the dental impression and a second assembly for forming the dental model, wherein the first assembly comprises: an impression post; a first coupler for coupling the impression post with a dental implant affixed within the mouth; and an impression cap for positioning on the impression post; and wherein the second assembly comprises: a model post; a second coupler for coupling the model post with a dental analog; and the impression cap. The impression cap comprises a first and second securing means, both for selectively securing the impression cap to the impression post and to the model post. In some embodiments the first assembly further comprises the dental implant. In some embodiments the second assembly further comprises the dental analog.

The first securing means is preferably a magnet disposed within the impression cap for securing to a magnetically attractable element. The magnetically attractable element is preferably the first coupler. Additionally or alternatively, the magnetically attractable element is the impression post.

The second securing means is at least one circumferential lip situated within the cavity of the impression cap for securing within at least one circumferential groove formed by the first coupler and the impression post.

In another embodiment, the second securing means is at least one circumferential lip situated within the cavity of the impression cap for securing within at least one circumferential groove formed by the second coupler and the model post.

Preferably, the diameter of the proximal end of the impression coupler is less than diameter of the proximal end of the model coupler.

The impression post comprises a first end, a second end and a central body portion, wherein the maximal diameter of the second end is greater than its height including the head of the coupler when assembled.

The present invention further provides a method for forming a dental impression and dental model comprising the following steps:
 a. affixing a dental implant in the bone within the mouth;
 b. providing the first assembly of claim 1;
 c. positioning the impression post within the dental implant;
 d. securing the impression post to the dental implant via the first coupler;
 e. positioning and securing the impression cap over the impression post;
 f. providing an impression tray at least partially filled with impression material, and immersing at least the impression cap within the impression material;
 g. waiting a predetermined amount of time for the impression material to harden;
 h. disengaging the impression cap from the impression post;
 i. removing the tray from the mouth;
 j. providing the second assembly of claim 1;
 k. inserting the model post into the dental analog;
 l. securing the model post to the dental analog via the second coupler;
 m. inserting the model post into the impression cap;
 n. positioning the dental analog into a tray at least partially filling it with liquid plaster;
 o. waiting a predetermined amount of time for the plaster to harden; and,
 p. disengaging the impression cap from the model post.

BRIEF DESCRIPTION OF THE FIGURES

To accomplish the above and related objects, the invention may be embodied in the form illustrated in the accompanying drawings, attention being called to the fact, however, that the drawings are illustrative only, and that changes may be made in the specific construction illustrated and described.

FIG. 1 shows an exploded perspective view of the first assembly of the present invention, for taking dental impressions;

FIG. 2 shows a side view of the impression post of FIG. 1, shown with the coupler disposed through the hollow longitudinal center of the impression post;

FIG. 3 shows the impression cap in a partially cut perspective view;

FIG. 7 shows an exploded perspective view of the second assembly of the present invention, for forming dental models;

FIG. 8 shows a side view of the model post of FIG. 7, shown with the coupler disposed through the hollow longitudinal center of the model post;

DETAILED DESCRIPTION OF THE PREFERRED EMBODIMENTS

Figure 4:
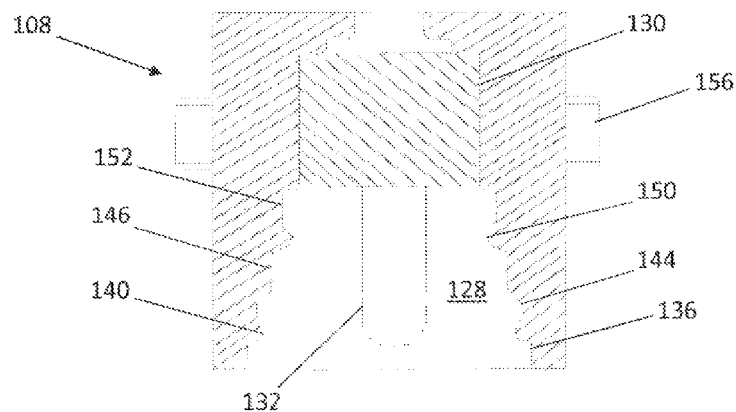
FIG. 4 shows a cross-sectional side view of the impression cap, taken along A-A of FIG. 1.

A preferred embodiment of the first assembly of the present invention, for taking dental impressions, is shown in FIG. 1 in an exploded perspective view, designated generally by numeral (100), and comprises an impression post (104), a coupler (106) for joining impression post (104) with a dental implant (102) previously affixed within a bone in the mouth of a patient, and an impression cap (108).

It is understood that it is common for dental implant (102) to be affixed within a bone in the mouth prior to the impression taking procedure, typically several months in advance. As such, in a preferred embodiment, first assembly (100) comprises impression post (104), coupler (106) and an impression cap (108), as described above, without dental implant (102). In an alternative embodiment, dental implant (102) is included in assembly (100).

Dental implant (102) comprises a standard sized dental implant known in the art, and chosen by the dental practitioner according to his needs. Impression post (104) shown in the figure comprises an essentially cylindrical body portion (110) and a first end (112) comprising a male portion for insertion into the well of the female end (114) of dental implant (102). In other embodiments (not shown), the dental implant comprises a male end for insertion into the well at the first end of the impression post. In the figure, first end (112) comprises a hexagonal shape for fitting into corresponding female end (114), although any suitable corresponding shapes may be used. Second end (116) of impression post (104) comprises an essentially cylindrical female portion for receiving coupler (106) as described herein below. As best seen in a side view of impression post (104) in FIG. 2, shown with coupler (106) disposed through the hollow longitudinal center (118) (see FIG. 1) of impression post (104), the outer circumference of second end (116) comprises a stepped curvature, as described in greater detail herein below.

In order to overcome some of the drawbacks associated with impression posts of the prior art described herein above, the length of impression post (104) is shorter than that of a typical prior art impression post. For instance, the length of the second end of a typical prior art impression post is 7 mm, whereas second end (116) of impression post (104) of the present invention is preferably 2-3 mm in length. In a preferred embodiment, the maximal diameter of the second end (116) is greater than its height (length) including the head of the coupler (124) when assembled. The reduced length reduces the difficulty in the withdrawal of the impression cap from the mouth as well as reduces the potential of shifting of impression cap (108) within the dental impression.

Referring to FIGS. 1 and 2, coupler (106) comprises an elongated member (120) having a threaded distal end (122) for securing within the well of dental implant (102) and a wide diameter proximal end (124) for sitting on the proximal surface (126) of second end (116) of impression post (104) (see FIG. 2). The outer diameter of proximal end (124) is larger than the inner diameter of hollow longitudinal center (118) of impression post (104). Coupler (106) is manufactured from a material attractable by a magnetic force, such as metals.

In an alternative embodiment (not shown) coupler (106) does not comprise wide diameter proximal end (124), rather, wide diameter proximal end (124) is integrally joined to second end (116) of impression post (104) at proximal surface (126), forming integral circumferential groove (154) as seen in FIG. 2 and described herein below. In a further alternative embodiment, the present invention does not comprise a coupler as described and shown herein. Instead, the coupler comprises mechanical clips for maintaining the connection between impression post (104) and dental implant (102) (not shown).

Referring to FIGS. 3 and 4, impression cap (108) is shown in a cross-sectional perspective view (see FIG. 3) and a cross-sectional side view, both taken along A-A of FIG. 1 (see FIG. 4). Impression cap (108) comprises a cavity (128) having at its base a mechanical force providing element (130), which, in a preferred embodiment comprises a magnet. The inner contour of a portion of cavity (128) comprises a combination of indentations and protrusions, as described in greater detail herein below. An elongated protrusion (132) extends longitudinally along opposing walls (only one shown in the figures) for slidingly fitting into the corresponding groove (134) in impression post (104), thereby enabling proper alignment of impression cap (108) with impression post (104).

Figure 6:
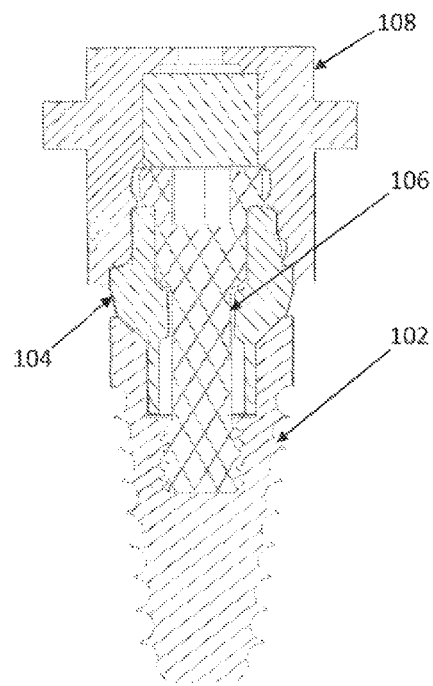
FIG. 6 shows an assembled cross-sectional view of the first assembly, cut longitudinally through the assembly.

With reference to FIGS. 2 and 4, when impression cap (108) is joined with impression post (104) (see also FIG. 6), the distal inner diameter (136) of cavity (128) fits tightly around the proximal outer diameter (138) of body portion (110) of impression post (104). Distal circumferential lip (140) protrudes radially inward, proximally from the distal end of impression cap (108), for sitting on proximal surface (142) of body portion (110). Lip (140) is preferably a partial ring, and may consist of more than one section. A circumferential depression (144) in cavity (128) is formed between lip (140) and distal side wall (146) of cavity for joining with the model post, as described herein below. Distal side wall (146) sits flush with the distal side wall (148) of second end (116) of impression post (104). Proximal circumferential lip (150), situated proximally from distal side wall (146) and distally from proximal side wall (152), protrudes radially inward, for sitting on proximal surface (126) of second end (116) of impression post (104), and essentially secure within the circumferential groove (154) formed between proximal surface (126) and wide diameter proximal end (124) of coupler (106). Lip (150) is preferably a partial ring, and may consist of more than one section.

Wide-diameter proximal end (124) of coupler (104) of first assembly (100) forms a shallow circumferential groove (154), which allows, a loose grasp on proximal lip (150). The main connecting force for securing impression cap (108) with impression post (104) is the magnetic force that attracts coupler (106) to magnet (130).

Figure 5:
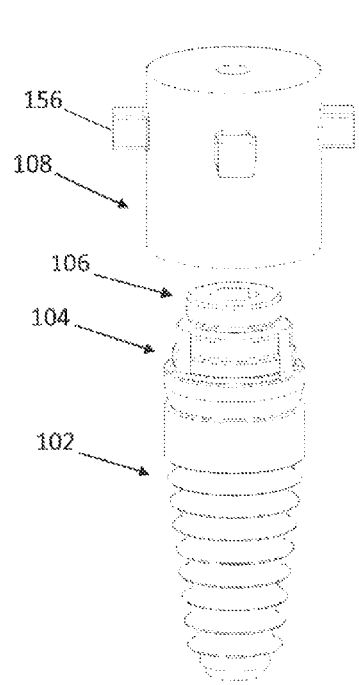
FIG. 5 shows the coupler inserted through the impression post and threadingly engaged with the dental implant, and the impression cap spaced apart therefrom.

As seen in FIG. 5, coupler (106) is inserted through impression post (104) and is threadingly engaged with dental implant (102) such that impression post (104) and dental implant (102) are securely joined. Impression cap (108) is shown spaced apart therefrom. Thus, when first assembly (100) is fully assembled, impression cap (108) is joined with impression post (104), which is joined to dental implant (102), as seen in an assembled cross-sectional view cut longitudinally through assembly, in FIG. 6.

Handles (156) protrude radially from the outer surface of impression cap (108) for securing impression cap (108) when embedded within the impression material used to form a dental impression, as described herein below. In the preferred embodiment, two handles (156) are spaced essentially equidistantly around the outer surface of impression cap (108), however any number of handles (156) may be present.

A preferred embodiment of the second assembly of the present invention, for forming dental models, is shown in FIG. 7 in an exploded perspective view, designated generally by numeral (200), and comprises a model post (204), a coupler (206) for joining impression model (204) with a dental analog (202), and impression cap (108).

In an alternative embodiment, dental analog (202) is included as part of second assembly (200).

Dental analog (202) comprises a standard sized dental analog known in the art, and chosen by the dental practitioner according to his needs. Dental analog (202) represents the dental implant (102) referred to in first assembly (100) when dental analog (202) is disposed within the stone dental model, described herein below. Distal portion (205) of analog (202) comprises an elongated cylindrical element (203), a portion of which is longitudinally cut out, for preventing analog rotation or shifting when in the dental model, as described herein below. Cylindrical rings (207) (preferably, at least one) having diameters wider than that of cylindrical element (203) are shown positioned around cylindrical element (203) for reinforcing the analog setting in the dental model, as described herein below.

Model post (204) comprises an essentially cylindrical body portion (210) and a first end (212) comprises a male portion for insertion into the well within the female end (214) of dental analog (202). In other embodiments (not shown), the dental implant comprises a male end for insertion into the well at the first end of the model post. In the figure, first end (212) comprises a hexagonal shape for fitting into corresponding female end (214), although any suitable corresponding shapes may be used. Second end (216) of model post (204) comprises a cylindrical female portion for receiving coupler (206) as described herein below. As best seen in a side view of model post (204) in FIG. 8, shown with coupler (206) disposed through the hollow longitudinal center (218) of model post (204), the outer circumference of second end (216) comprises a stepped curvature, as described further herein below.

Referring to FIGS. 7 and 8, second assembly coupler (206) is shown in second assembly (200) having an essentially identical structure as that of first assembly coupler (106) of first assembly (100), mutatis mutandis. However, the wide diameter proximal end (224) of coupler (206) is larger than that of wide diameter proximal end (124) of coupler (106) of first assembly (100), as described further herein below.

Coupler (206) is an elongated member (220) having a threaded distal end (222) for securing to the inside of dental analog (202) and a wide diameter proximal end (224) for sitting on the proximal surface (226) of second end (216) of model post (204) (see FIG. 8). The outer diameter of proximal end (224) is larger than the inner diameter of hollow longitudinal center (218) of model post (204).

Impression cap (108) is shown in second assembly (200) as the same component used as the impression cap (108) of first assembly (100), and described herein above. Elongated protrusion (132) extends longitudinally along opposing walls (only one shown in the figure) for slidingly fitting into the corresponding groove (234) in impression post (104), thereby enabling proper alignment of impression cap (108) with model post (204).

Referring to FIGS. 4 and 8, when impression cap (108) is joined with model post (204), the distal inner diameter (136) of cavity (128) fits tightly around the proximal outer diameter (238) of body portion (210) of model post (204). Distal circumferential lip (140) protrudes radially inward, proximally from the distal tip of impression cap (108), for sitting on proximal surface (242) of body portion (210). A circumferential depression (144) in cavity (128) is formed between lip (140) and distal side wall (146) of cavity, in which circumferential ring (243) around second end (216) of model post (204) is disposed. Distal side wall (146) sits flush with the proximal side wall (248) of second end (216) of model post (204). Proximal circumferential lip (150), situated proximally from distal side wall (146) and distally from proximal side wall (152), protrudes radially inward, for sitting on proximal surface (226) of second end (216) of model post (204), and essentially secure within the circumferential groove formed (254) between proximal surface (226) and wide diameter proximal end (224) of coupler (206). Lip (150) is preferably a partial ring, and may consist of more than one section.

As compared with the smaller diameter of wide-diameter proximal end (124) of coupler (104) of first assembly (100), the larger diameter wide-diameter proximal end (224) of coupler (204), forms a deeper circumferential groove (254) than groove (154) formed in first assembly (100) (see FIG. 2). This is significant because the deeper groove (254) enables proximal lip (150) to be held tightly within groove (254), in contrast with the shallow groove (154) of first assembly (100) which allows a looser grasp on proximal lip (150).

In addition to the secured distal and proximal lips (140), (150), impression cap (108) and model post (204) are secured together by the magnetic force that attracts coupler (206) to magnet (130). Optionally, impression cap (108) does not comprise a magnet, and impression cap (108) is secured to model post via the grasp of distal and proximal lips (140), (150).

Figure 9:
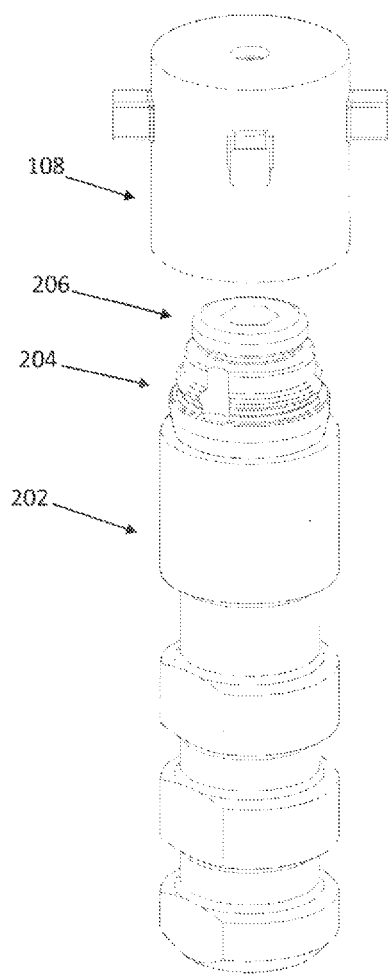
FIG. 9 shows the coupler inserted through the model post and threadingly engaged with the dental analog and the impression cap spaced apart therefrom.
Figure 10:
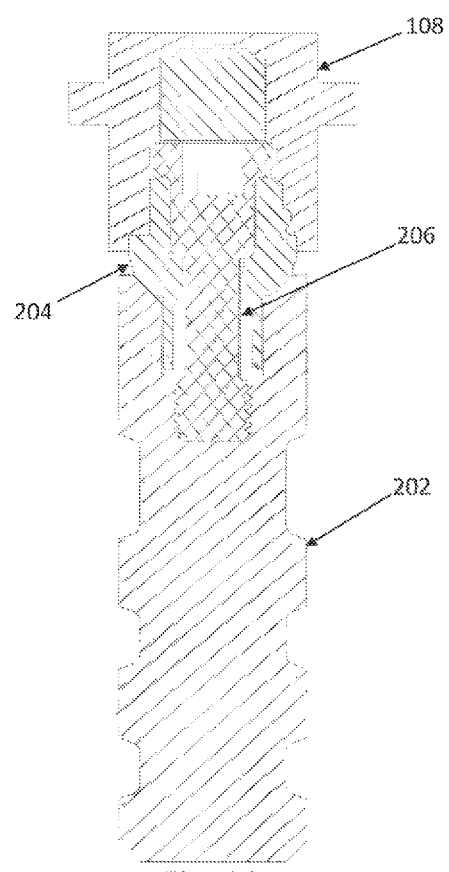
FIG. 10 shows an assembled cross-sectional view of the second assembly, cut longitudinally through the assembly.

As seen in FIG. 9, coupler (206) is inserted through model post (204) and threadingly engaged with dental analog (202) such that model post (204) and dental analog (202) are securely joined. Impression cap (108) is shown spaced apart therefrom. Thus, when second assembly (200) is fully assembled, impression cap (108) is joined with model post (204), which is joined to dental analog (202), as seen in an assembled cross-sectional view cut longitudinally through assembly, in FIG. 10.

The method of the present invention for taking dental impressions and forming models using the kit of the present invention is described herein below and comprises the following steps:

First assembly (100) is provided for forming a dental impression. Dental implant (102) is either previously affixed within a bone in the mouth or requiring affixing within a bone in the mouth. Impression post (104) is positioned within dental implant (102) and secured thereto via coupler (106). Impression cap (108) is then positioned on, and secured to impression post (104), as described herein above. An impression tray, at least partially filled with impression material such as silicon is positioned over impression post (104) and at least impression cap (108) is immersed within the impression material. After waiting a predetermined amount of time, impression material hardens with impression cap embedded therein. Alternatively, impression material is injected around the impression cap to take an impression.

Figure 11:
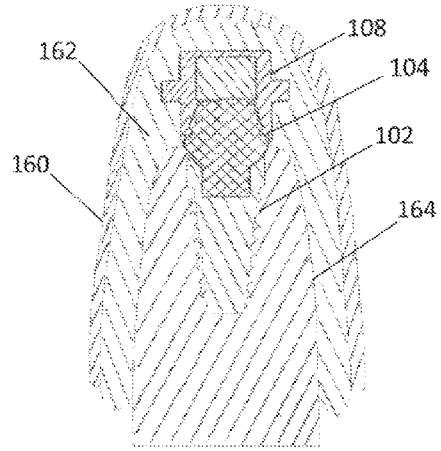
FIG. 11 shows a cross-sectional front view of an impression tray with impression material positioned within the mouth.

To schematically illustrate the state of the process at this point, FIG. 11 shows a cross-sectional front view of an impression tray (160) with impression material (162) surrounding impression cap (108) secured to impression post (104), with dental implant (102) positioned within bone (164).

After hardening of the impression material, impression cap (108) is disengaged from impression post (104) by removing the tray from the mouth. See FIG. 12, which schematically illustrates impression tray (160) with impression material (162) and embedded impression cap (108) disengaged from the impression post and removed from the mouth.

Typically, the process until this point is performed by a dental practitioner such as a dentist, and the remainder of the process is typically performed by a dental technician, although any properly trained dental professional may perform any or all of the steps in the process.

Second assembly (200) is provided for forming a dental model. Model post (204) is inserted into dental analog (202) and coupler (206) secures model post (204) thereto. Model post (204) is inserted into impression cap (108) and dental analog (202) is positioned within a tray, and the tray is at least partially filled with liquid plaster. After waiting a predetermined amount of time, the plaster material hardens, forming a stone dental model.

Figure 12:
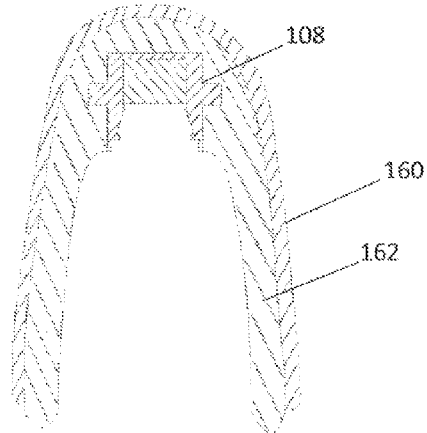
FIG. 12 shows a cross-sectional front view of an impression tray with impression material removed from the mouth with an impression cap embedded therein.
Figure 13:
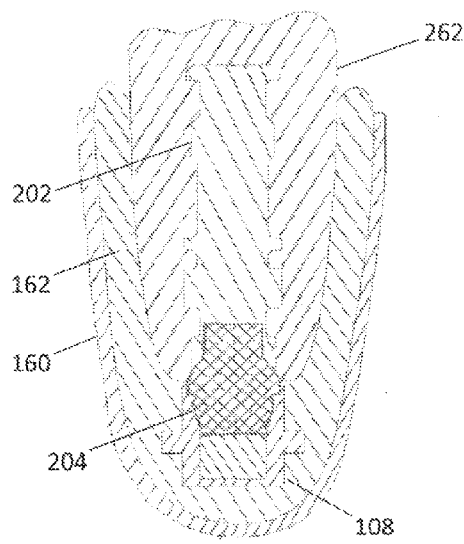
FIG. 13 shows the cross-sectional front view of FIG. 12, showing the impression tray with impression material, and the impression cap embedded therein, and a stone dental model formed around the dental analog.

To schematically illustrate the state of the process at this point, FIG. 13 shows the cross-sectional front view of FIG. 12, showing impression tray (160) with impression material (162) and embedded impression cap (108), in this figure, surrounding hardened plaster (262), forming a stone dental model and dental analog (202) embedded therein.

Figure 14:
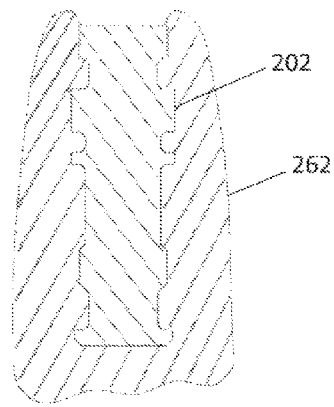
FIG. 14 shows the stone dental model and embedded dental analog disengaged from the impression cap.

After hardening of the plaster, impression cap (108) is disengaged from model post (204). See FIG. 14, which schematically illustrates stone dental model (262) and embedded dental analog (202) disengaged from impression cap (108) and model post (204) of FIG. 13.

It should be noted that the method described herein is described for illustrative purposes only as utilizing a single kit comprising the first and second assemblies for forming a single dental impression and a single corresponding dental model of the single dental impression. However, it is understood that the present invention is also intended to utilize multiple kits simultaneously in order to form multiple dental impressions and a corresponding dental model of the multiple dental impressions, mutatis mutandis.

It is understood that the above description of the embodiments of the present invention are for illustrative purposes only, and is not meant to be exhaustive or to limit the invention to the precise form or forms disclosed, as many modifications and variations are possible. Such modifications and variations are intended to be included within the scope of the present invention as defined by the accompanying claims.

The invention claimed is:

1. A kit for use in the process of taking a dental impression and forming a dental model, said kit comprising a first assembly for forming said dental impression and a second assembly for forming said dental model, wherein said first assembly comprises:
   a. an impression post;
   b. a first coupler for coupling said impression post with a dental implant affixed within the mouth; and
   c. an impression cap for positioning on said impression post;

and wherein said second assembly comprises:
   a. a model post;
   b. a second coupler for coupling said model post with a dental analog; and
   c. said impression cap, where said impression cap comprises a first and second securing means, both for selectively securing said impression cap to said impression post and to said model post.

2. The kit of claim 1, wherein the first assembly further comprises the dental implant.

3. The kit of claim 1, wherein the second assembly further comprises the dental analog.

4. The kit of claim 1, wherein the first securing means is a magnet disposed within the impression cap for securing to a magnetically attractable element.

5. The kit of claim 4, wherein the magnetically attractable element is the first coupler.

6. The kit of claim 4, wherein the magnetically attractable element is the impression post.

7. The kit of claim 1, wherein the second securing means is at least one circumferential lip situated within the cavity of the impression cap for securing within at least one circumferential groove formed by the first coupler and the impression post.

8. The kit of claim 1, wherein the second securing means is at least one circumferential lip situated within the cavity of the impression cap for securing within at least one circumferential groove formed by the second coupler and the model post.

9. The kit of claim 1, wherein the diameter of the proximal end of the impression coupler is less than diameter of the proximal end of the model coupler.

10. The kit of claim 1, wherein the impression post comprises a first end, a second end and a central body portion, wherein the maximal diameter of the second end is greater than its height including the head of the coupler when assembled.

11. A method for forming a dental impression and dental model comprising the following steps:
 a. affixing a dental implant in the bone within the mouth;
 b. providing the first assembly of claim 1;
 c. positioning the impression post within said dental implant;
 d. securing said impression post to said dental implant via the first coupler;
 e. positioning and securing the impression cap over said impression post;
 f. providing an impression tray at least partially filled with impression material, and immersing at least said impression cap within said impression material;
 g. waiting a predetermined amount of time for said impression material to harden;
 h. disengaging said impression cap from said impression post;
 i. removing said tray from said mouth;
 j. providing the second assembly of claim 1;
 k. inserting the model post into the dental analog;
 l. securing said model post to said dental analog via the second coupler;
 m. inserting said model post into said impression cap;
 n. positioning said dental analog into a tray at least partially filling it with liquid plaster;
 o. waiting a predetermined amount of time for said plaster to harden; and
 p. disengaging said impression cap from said model post.

* * * * *